United States Patent [19]

Celmer et al.

[11] 4,031,206

[45] June 21, 1977

[54] ANTIBIOTICS PRODUCED BY SPECIES OF PSEUDONOCARDIA

[75] Inventors: Walter D. Celmer, New London; Walter P. Cullen, East Lyme; Charles E. Moppett, Mystic; John B. Routien, Lyme, all of Conn.; Riichiro Shibakawa, Handa; Junsuke Tone, Chita, both of Japan

[73] Assignee: Pfizer Inc., New York, N.Y.

[22] Filed: Feb. 4, 1976

[21] Appl. No.: 655,075

[52] U.S. Cl. .............................. 424/117; 424/115; 195/81

[51] Int. Cl.² ....................................... A61K 35/70

[58] Field of Search .............. 424/117, 115; 195/81

[56] References Cited

UNITED STATES PATENTS 3,689,639  9/1972  Bergy et al. ................... 424/117

Primary Examiner—Jerome D. Goldberg
Attorney, Agent, or Firm—Connolly and Hutz

[57] ABSTRACT

A new species of *Pseudonocardia*, designated *Pseudonocardia fastidiosa* sp. nov. Routein, when subjected to submerged aerobic fermentation, produces two new antibiotics. Methods for the recovery and purification of these antibiotics are described and some of their antimicrobial properties are outlined.

3 Claims, 2 Drawing Figures

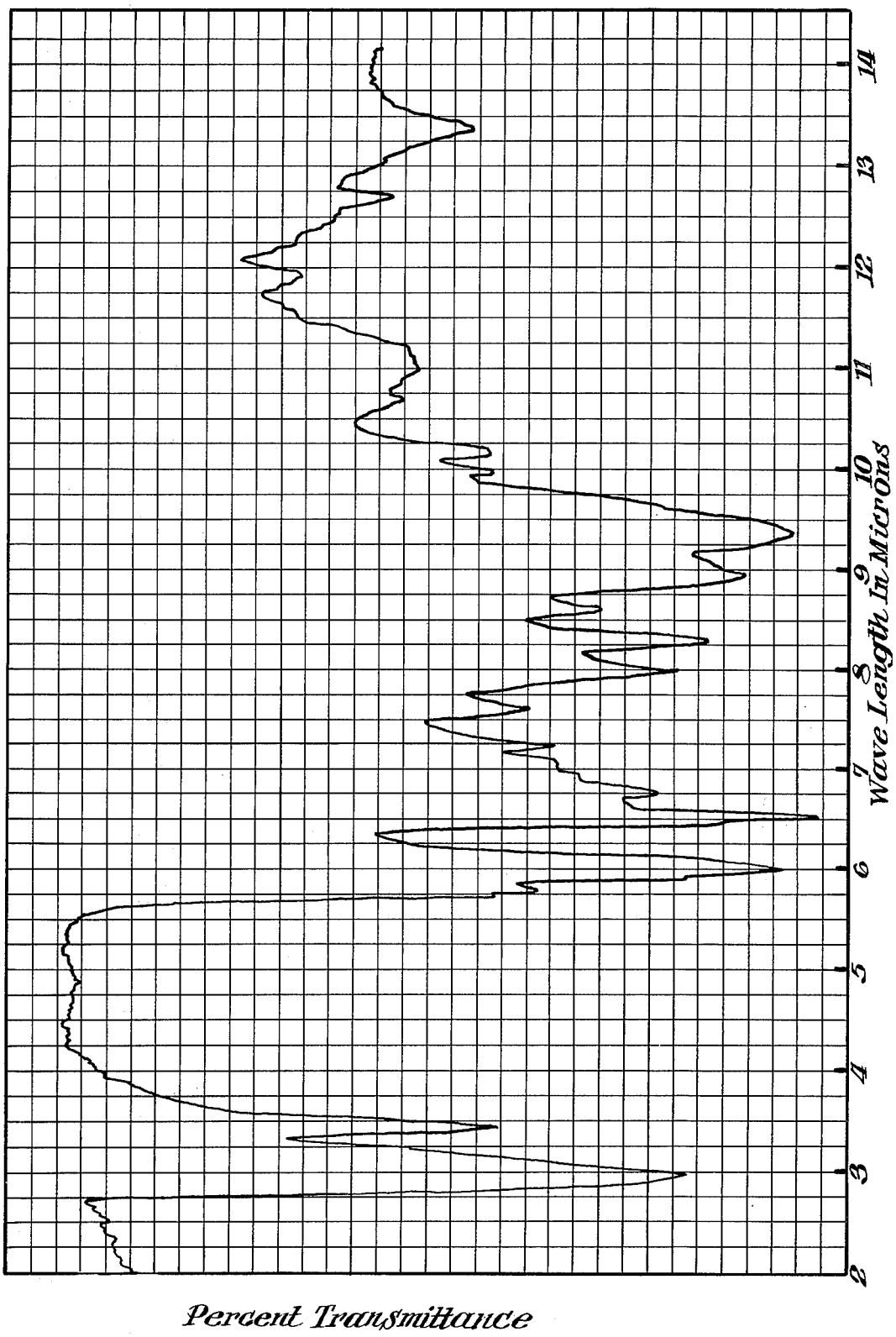

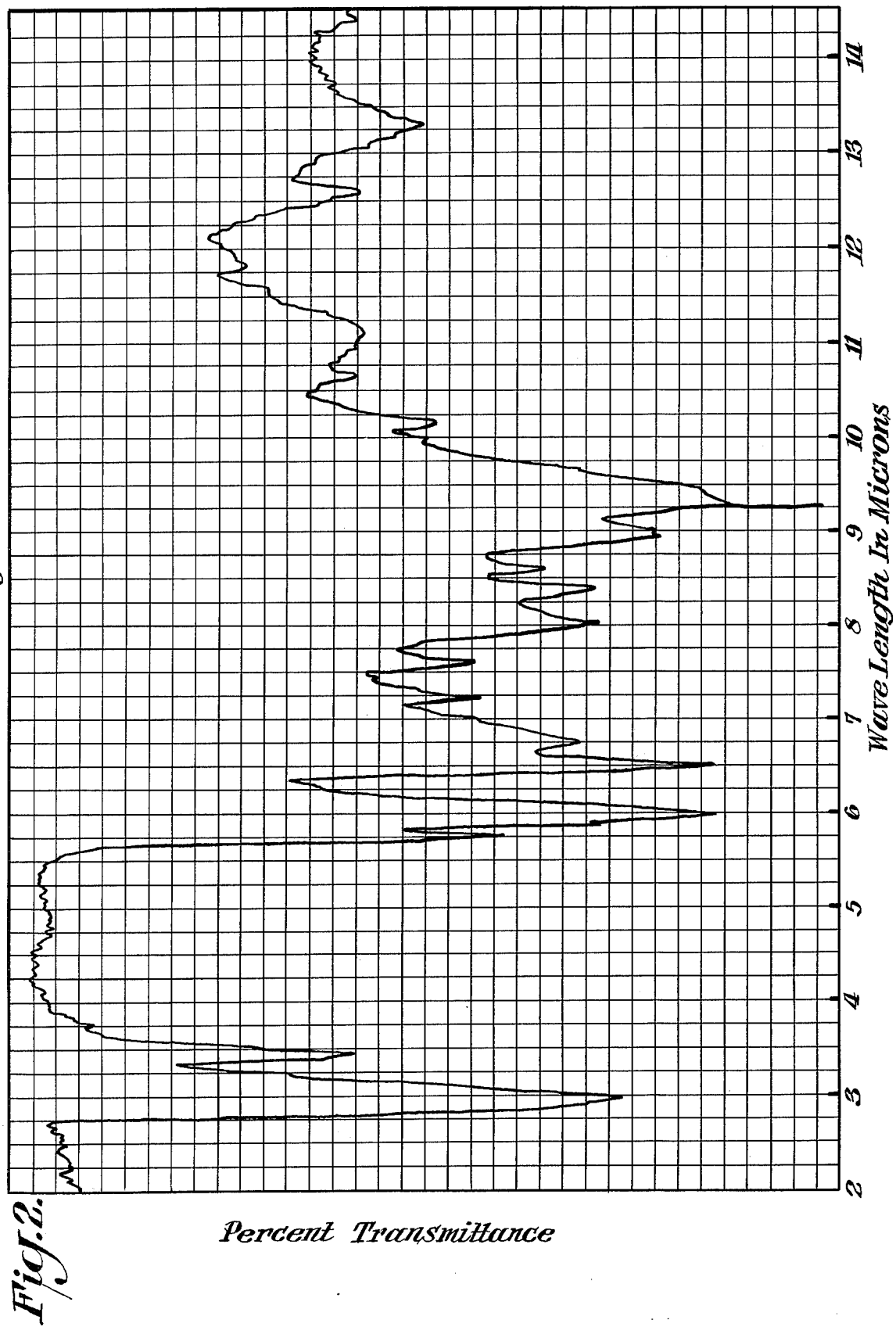

ANTIBIOTICS PRODUCED BY SPECIES OF PSEUDONOCARDIA

BACKGROUND OF THE INVENTION

The search for new antibiotics produced by soil microorganisms has encompassed the screening of various genera of bacteria, higher bacteria and fungi including many species within each genus and many strains within each species.

Among the microorganisms that have not received must attention are those that belong to the genus *Pseudonocardia*. This genus and the genus *Nocardia* belong to the Order Actinomycetales with the genus *Pseudonocardia* differentiated from *Nocardia* by the production in the aerial mycelium of long unbranched chains of spores by acropetal development and the zig-zag pattern of growth of some hypae.

SUMMARY OF THE INVENTION

This invention is concerned with Compounds 41,043 and 41,494, macrobicyclic peptide antibiotics produced under submerged aerobic fermentation conditions by *Pseudonocardia fastidiosa* sp. nov. Routien ATCC 31181.

DETAILED DESCRIPTION OF THE INVENTION

The microorganism useful for the preparation of the antibiotics of this invention was isolated from a soil sample from Egypt. This culture (Pfizer F.D. 25028), designated *Pseudonocardia fastidiosa* sp. nov. Routien, has been deposited in The American Type Culture Collection, Rockville, Md. as the type culture under their accession number ATCC 31181. The permanency of the deposit and ready accessibiltiy thereto by the public are afforded in the event the patent is granted. Access to the culture is available during pendency of the application under Rule 14 and 35 USC 112. All restrictions on the availability to the public of the culture deposited will be irrevocably removed upon granting of the patent.

The culture was incubated at 28° C. unless otherwise stated and records of results were made after suitable incubation time. Colors were recorded in general terms and by names of Ridgway's *Color Standards and Nomenclature*, 1912.

The media or tests and appropriate references are as follows:

1. Tap water agar — 2% agar plus tap water.
2. Potato-carrot agar — M.P. Lechevalier, Jr. Lab. and Clinical Med. 71:934-944, 1968. Use only 30 g potatoes and 2.5 g carrots and 20 g agar per liter.
3a. Potato Dextrose Agar (Difco).
3b. Potato Dextrose Agar made from infusion of 100 g peeled potatoes per liter and 10 g glucose per liter, pH 7.0.
3c. Potato Dextrose Agar made as in 3b but pH of 5.5 like that of 3a.
4. Glycerol Asparagine Agar — Waksman, S. A. The Actinomycetes, Vol. II, medium 3 on p. 328, 1961.
5. Yeast Extract-Malt Extract Agar — T. G. Pridham et al. Antibiotics Ann. 1956/57, pp. 947-953.
6. Potato plugs.
7. Aerobiosis test — ATCC medium 172 on p. 235 of Americal Type Culture Catalogue, 10th ed., 1972.
8. Half strength skim milk agar (Difco Skim Milk).
9. Czapek-Sucrose Agar — Waksman, S. A., The Actinomycetes, Vol. II, medium 1, page 328, 1961.
10. Glucose Yeast Extract Agar — Waksman, S. A., The Actinomycetes, Vol. II, medium 29, page 331, 1961.
11. Gelatin — R. E. Gordon and J. M. Mihm, Jr. Bact. 73:15-27, 1957.
12. Starch Agar — Ibid.
13. Inorganic Salts Starch Agar — ISP medium No. 4.
14. Skim Milk.
15. Cellulose
    a. H. L. Jensen, Proc. Linnean Soc. N. S. Wales 55:231-248, 1930.
    b. M. Levine and H. W. Schoenlein, A Compilation of Culture Media, medium no. 2511, 1930.
16. Temperature Range — ATCC medium 172 from Americal Type Culture Catalogue, 10th ed., p. 235, 1972.
17. Tryptone Yeast Extract Broth — T. G. Pridham and D. Gottlieb, Jr. Bact. 56:107-114, 1948.
18. Peptone Iron Agar (Difco) with Lead Acetate Strips.
19. Oatmeal Agar — ISP medium 3.
20. Nitrate Reduction
    a. Dextrose Nitrate Broth — Waksman, S.A. The Actinomycetes, Vol. II, medium no 1, page 328, 1961 but 3 g dextrose substituted for 30 g sucrose and agar omitted.
    b. Organic Nitrate Broth
       Ibid, medium no. 37, p. 332.
21. Hyphal Study — G. M. Luedemann and B. C. Brodsky. Antimicrobial Agents and Chemotherapy, 1964, pp. 47-52.
22a. Carbohydrate Utilization — ISP medium no. 9.
22b. Carbohydrate Utilization — ISP medium No. 4 with various carbon sources replacing the starch.

The description of *Pseudonocardia fastidiosa* sp. nov. Routien:

Inorganic Salts Starch Agar — growth moderate, flat with slight roughening of surface; growth yellow (Ridgway's Maize Yellow to Buff Yellow) with pale pink aerial mycelium (white for two weeks but pink at end of four weeks); reverse yellow; pale yellow soluble pigment, no odor.

Czapek Sucrose — growth good, slightly raised, somewhat roughened; growth yellow (Maize Yellow to Buff Yellow) with white to pale pink aerial mycelium along edge after four weeks; reverse yellow; yellow soluble pigment; weak disagreeable odor.

Glycerol Asparagine Agar — growth poor, thin, flat, smooth, yellow (near Pale Chalcedony Yellow); no aerial mycelium; reverse pale yellow; very pale yellow soluble pigment; no odor (4 weeks' reading).

Gelatin — growth good, somewhat raised and with some roughening of surface, dull yellow color; no aerial mycelium; reverse brownish yellow; yellow soluble pigment; no odor (4 weeks' reading).

Starch Agar — growth excellent, raised, roughened, yellowish orange; no aerial mycelium; reverse dark orange-yellow to brownish-yellow; brownish-yellow soluble pigment; no odor (4 weeks' reading).

Glucose Yeast Extract Agar — growth moderate, thin, flat, slightly roughened; growth shiny, yellow; small sectors of white aerial mycelium along edge of growth; reverse yellow; yellow soluble pigment; no odor (4 weeks' reading).

Yeast Extract — Malt Extract Agar — growth good, somewhat raised, finely wrinkled, dull yellow to pale salmon color (Ochraceous Buff to Antimony Yellow) at edge; no aerial mycelium; reverse dull yellow; slight brownish-yellow soluble pigment; weak disagreeable odor (4 weeks' reading).

Potato Dextrose Agar — no growth on Difco medium but good growth on media 3b and 3c, cream colored, naked; reverse cream-colored; no soluble pigment.

Oatmeal Agar — growth moderate, flat, pale yellow to cream-colored; no aerial mycelium; reverse pale yellow; pale yellow soluble pigment; no odor (4 weeks' reading).

Tap Water Agar — growth very poor, thin, flat, very pale yellow; no aerial mycelium; reverse nearly colorless; no soluble pigment; no odor (4 weeks' reading).

Potato-Carrot Agar — growth poor, thin, flat, very faint yellow color in thicker portions of growth; outgrowths of white aerial mycelium along edge; reverse very pale yellow; pale yellow soluble pigment; no odor (4weeks' reading.).

Half-Strength Skim Milk Agar — growth moderate, flat, smooth except for some wrinkling at edge, brown (near Cinnamon Brown to Russet); no aerial mycelium; reverse brown; brown soluble pigment; disagreeable odor (4 weeks' reading).

Biochemical Properties — starch hydrolyzed (3 days); gelatin liquefied (3 days); no melanin produced in tryptone yeast extract broth or peptone iron agar; no $H_2S$ produced; nitrate reduced quickly (3 days) to nitrite in both dextrose nitrate broth and organic nitrate broth; growth (14–21 days) without digestion on Jensen's Cellulose medium but no growth on medium from Levine and Schoenlein; milk partially coagulated and slight peptonization (14–21 days); aerobic, no growth on any carbohydrate tested when ISP medium No. 9 was used byt on ISP medium No. 4 minus starch the culture utilized glucose, arabinose, fructose, raffinose (weakly), starch and xylose but failed to utilize inositol, mannitol and rhamnose.

Vegatative Growth — substrate hyphae 0.5–10 $\mu$ wide, often showing zig-zag shape; branches developed at right angles or acute angles, the former often having a terminal, oval to pyriform swelling (1.6–2.0 $\mu$ wide) which by further growth resulted in a thin hypha extending outward from the swollen part and thus producing intercalary swellings.

Aerial Mycelium — when freshly isolated the culture produced a flat mass of white aerial mycelium with an abundance of long chains of spore-like segments that later divided into two spores of equal size. Segments were produced by acropetal budding and sometimes thinner branches developed from near the apparent tip of a segment. There was sometimes a slight zig-zag appearance to the chains. The longer segments were rod-shaped, mostly straight 9–10 × 1.0 $\mu$. Division of each into two smaller bodies as the culture became older produced spores about 4.5 × 1.2 $\mu$, slightly wider than the parent segments. Scanning electron microscope study show the spores to have a smooth surface.

The culture shows so many properties different from described species of *Pseudonocardia* that it was considered to be a new species. Because it did not grow on the inorganic salts medium normally used for cultures of actinomycetes, it was named *Pseudonocardia fastidiosa*.

Cultivation of the *Pseudonocardia* culture preferably takes place in nutrient media at a temperature of about 28°–36° C., and under aerobic, submerged conditions with agitation. Nutrient media which are useful for such purposes include a source of assimilable carbon such as sugars, starch, glycerol and molasses; a source of organic nitrogen such as fish meal, casein, enzymatic digest of casein, meat meal, wheat gluten, cottonseed meal, soybean meal and peanut meal. A source of growth substances such as distillers' solubles and/or yeast extract as well as salts such as sodium chloride, ammonium acetate, ammonium sulfate, potassium phosphate and trace minerals such as iron, magnesium, zinc, cobalt and manganese may also be utilized with advantageous results. If excessive foaming is encountered during fermentation, antifoam agents such as vegetable oils or silicones may be added to the fermentation medium. The pH of the fermentation tends to remain rather constant but if variations are encountered, a buffering agent such as calcium carbonate may also be added to the medium. Aeration of the medium in tanks for submerged growth is preferably maintained at the rate of about ½ to 2 volumes of free air per volume of broth per minute. Agitation may be maintained by means of agitators generally familiar to those in the fermentation indusry. Aseptic conditions must, of course, be maintained through the transfer of the microoganism and throughout its growth.

Inoculum for the preparation of the antibiotic may be obtained by employing growth from slants or Roux bottles of *P. fastidiosa* on such agar media as ATCC Medium 172 to which previous reference was made. The growth may be used to inoculate either shake flasks or inoculum tanks, or alternatively, the inoculum tanks may be seeded from the shake flasks. The growth of the microorganism usually reaches its maximum in about 2 or 3 days. However, variations in the equipment used, aeration, rate of stirring, etc. may affect the speed with which the maximum growth is reached. In general, the fermentation is conducted until substantial antimicrobial activity is imparted to the medium, a period of from about 24 hours to about 4 days being sufficient for most purposes.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency.

Thin-layer chromatogrpahy employing silica gel is a useful tool for analyzing the antibiotics produced by *Pseudonocardia fastidiosa* in the fermentation media and the composition of crude and purified materials extracted from fermentation broths. Silica gel plates are employed with a developing system of chloroform: ethanol (85:15 -v/v) and observing the developed plates under 254 nm light. Two antibiotics, Compound 41,043 (major, less polar) and Compound 41,494 (minor, more polar) are apparent by these techniques. When desired, bioautographic detection of the antibiotic components may be accomplished by means of an overlay of a thin layer of agar seeded with a sensitive strain of *Staphylococcus aureus* or other sensitive organism on the developed silica gel chromatograms.

The antibiotics of the present invention are macrobicyclic peptides and belong in the general class of similar, previously reported antibiotics: Multhiomycin, The Journal of Antibiotics, 23, No. 5, 231 (1970); Thiopeptin, The Journal of Antibiotics, 23, No. 3, 113 (1970); Thiostrepton, Antibiotics Annual, 560 (1955–1956);

Siomycin, The Journal of Antibiotics, Ser. A, 14, 255 (1961); and A-59, The Journal of Antibiotics, Ser. A, 14, 194 (1961).

Compounds 41,043 and 41,494 may be recovered and purified by the methods reported for other macrobicyclic peptides which include solvent extraction and column chromatography or combinations thereof. Organic solvents such as n-butanol, methylisobutyl ketone, ethyl acetate and chlorinated hydrocarbons may be used to extract the antibiotics from whole or clarified fermentation broth at pH ranges from 4.0 to 10.0. Alternatively, the separated mycelium is extracted with methanol, the methanol extract concentrated in vacuo and the methanol concentrate, diluted to one-tenth its original volume with water, is twice extracted with one-third volumes of methylisobutyl ketone. The solvent is concentrated to a thin syrup and the antibiotics precipitated with heptane. The crude antibiotics are dissolved in acetone and chromatographed on a silica gel column developed with hexane, chloroform, chloroform:ethanol (98:2 to 90:10% v/v) and acetone:chloroform (50:50% v/v).

The present invention includes within its scope the dilute forms and crude concentrates of the mixture of antibiotics and the individual crude and purified antibiotic components. All of these products are useful in combatting microorganisms such as *Sytreptococcus pneumoniae*, *Streptococcus pyogenes* and *Staphylococcus aureus*. In addition they are useful as disinfectants against such microorganisms and as an aid in the purification of mixed cultures for medical, diagnostic and biological research purposes.

Table I illustrates the antibacterial spectra of the antibiotic components. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic (in micrograms/ml) at which the microorganism failed to grow. The tests were conducted under standarized conditions as described in Proc. Soc. Exp. Biol. & Med., 122, 1107 (1966).

Table I

| Organism | | Compound 41,494 | Compound 41,043 |
|---|---|---|---|
| *Staphylococcus aureus* | 01A005 | 0.78 | 0.20 |
| | 01A052 | 0.78 | 0.39 |
| | 01A109 | 0.78 | 0.39 |
| | 01A110 | 0.78 | 0.39 |
| | 01A111 | 0.78 | 0.20 |
| | 01A087 | 0.78 | 0.39 |
| | 01A400 | 0.78 | 0.39 |
| *Streptococcus faecalis* | 02A006 | <0.10 | 0.39 |
| *Streptococcus pyogenes* | 02C203 | <0.10 | <0.10 |
| *Mycobacterium smegmatis* | 05A001 | 100 | 50 |
| *Bacillus subtilis* | 06A001 | 0.20 | <0.10 |
| *Escherichia coli* | 51A229 | >200 | >200 |
| | 51A266 | 200 | 200 |
| | 51A125 | 200 | 200 |
| *Pseudomonas aeruginosa* | 52A104 | >200 | >200 |
| | 52A440 | 200 | 200 |
| *Klebsiella pneumoniae* | 53A009 | >200 | >200 |
| | 53A031 | 200 | 200 |
| *Proteus mirabilis* | 57C064 | >200 | >200 |
| *Proteus morgani* | 57G001 | >200 | >200 |
| *Salmonella cholerae-suis* | 58B242 | >200 | >200 |
| *Salmonella typhi-murium* | 58D009 | >200 | >200 |
| | 58D013-C | 200 | 200 |
| *Pasteurella multocida* | 59A001 | >200 | >200 |
| *Serratia marcescens* | 63A017 | >200 | >200 |
| *Enterobacter aerogenes* | 67A040 | >200 | >200 |
| *Enterobacter cloacae* | 67B003 | >200 | >200 |
| *Neisseria sicca* | 66C000 | <0.10 | <0.10 |

In vivo protection afforded by Compound 41,043 against mice experimentally infected with *Staphylococcus aureus* 01A005 is shown in Table II.

Table II

| Compound 41,043 Dose (mg/kg) | % Protection |
|---|---|
| 400 (subcutaneous) | 80 |
| 200 (subcutaneous) | 60 |
| 100 (subcutaneous) | 40 |
| 400 (oral) | 0 |

The antibiotics of this invention can be administered via the oral or parenteral routes for the treatment in animals, including humans, of pneumococcal, streptococcal, staphylococcal, tubercular and other antibiotic-sensitive infections. In general, these antibiotics are most desirably administered in daily oral doses of 0.5–1 gram or parenteral injections of 100 to 500 mg., depending on the type and severity of the infection and weight of the subject being treated.

The compounds of this invention may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purposes of parenteral administration, solutions of these antibiotics in sesame or peanut oil or in aqueous propylene glycol may be employed.

The following examples are given to more fully illustrate the invention. It is to be understood that these examples are for illustrative purposes only and that the invention is not meant to be limited to the specific details of the examples.

EXAMPLE I

A sterile aqueous medium having the following composition was prepared:

| Ingredient | Grams/liter |
|---|---|
| Glucose | 10 |
| Starch | 20 |
| Yeast extract | 5 |
| Enzymatic digest of casein | 5 |
| Meat meal | 5 |
| $K_2HPO_4$ | 0.5 |
| $CoCl_2 \cdot 6H_2O$ | 0.002 |
| $CaCO_3$ | 4 |
| pH - 7.1–7.2 | |

Cells from a slant culture of *Pseudonocardia fastidiosa* ATCC 31181 were transferred to each of a number of 300 ml Erlenmeyer flasks each containing 50 ml of the above medium and shaken at 28° C. on a rotary shaker for 3 to 4 days.

A sterile aqueous medium having the following composition was prepared:

| Ingredient | Grams/liter |
|---|---|
| Glucose | 10 |
| Enzymatic digest of casein | 5 |
| Yeast extract | 5 |
| Starch | 20 |
| $CaCO_3$ | 1 |
| $CoCl_2 \cdot 6H_2O$ | 0.002 |
| pH - 7.1 ± 0.1 | |

Fermentors containing two liters of the above described sterile medium were seeded with 5% v/v of grown inoculum. The temperature was maintained at 28° to 36° C. and the broth was stirred at 1700 r.p.m. and aerated at the rate of about one volume of air per volume of broth per minute. After about 40 to 60 hours, clarified broth or whole broth was twice extracted with one-third to one-half volume of methylisobutyl ketone, the solvent extract concentrated in vacuo and the antibiotics precipitated by the addition of n-heptane.

EXAMPLE II

The fermentation process of Example I was repeated. The mycelium was separated from the whole broth and slurried with methanol. The methanol extract was concentrated in vacuo to < 1/10 volume. The concentrate was diluted up to one-tenth to one-fifth of its original volume with water, the pH adjusted to 6.0 and twice extracted with one-third volume methylisobutyl ketone. The solvent extract was concentrated under vacuum to a syrup and the antibiotics precipitated by the addition of n-heptane.

EXAMPLE III

The fermentation process of Example I was repeated. About 10% of the grown inoculum was used to inoculate two 250 gallon fermentors each containing 100 gallons of the medium of Example I. The tanks were fermented for two to four days at which time sufficient volume of broth was used to provide a 10% inoculum for two 1500 gallon fermentors each containing 1000 gallons of the medium of Example I. The fermentation was conducted at a temperature of 30° C and an aeration rate of one volume of air per volume of broth per minute. After substantial antibiotic activity was obtained (approximately 48 to 72 hours), the whole fermentation broth was adjusted to pH 6.0 with 50% sulfuric acid and extracted with 400 gallons of methylisobutyl ketone on a Podbelniak. The solvent was removed in vacuo and the antibiotics contained within the concentrate were precipitated by the addition of 4 volumes of n-heptane. The precipitated solids (420 grams) were collected by filtration, washed with n-heptane and dried in vacuo.

The antibiotic complex (100 grams) was dissolved in the minimum volume of acetone and treated with 500 grams of silica gel $PF_{254}$ (E. Merck, Darmstadt, Germany). The solvent was removed in vacuo and the residue treated with hexane to give a mobile slurry which was then added to a sintered glass funnel containing a bed of about 100 grams of silica gel 60 (E. Merck, Darmstadt, Germany) topped with a bed of about 100 grams of silica gel $PF_{254}$. The antibiotics were then eluted with hexane, chloroform, chloroform:ethanol (98:2 to 90:10% v/v) and acetone:chloroform (50:50% v/v). All fractions were assayed by thin-layer chromatography and bioassay and appropriate fractions were pooled. Those fractions rich in Compound 41,043 (Chloroform:ethanol — 95:5 to 93:7% v/v, 59 grams) were further processed by chromatography on silca gel $PF_{254}$ eluting with chloroform:ethanol (90:10% v/v). 5.0 Gram portions of this material were readily handled on a 2.54 cm silica gel column. All cuts were assayed by thin-layer chromatography and the appropriate fractions combined and evaporated in vacuo to a amorphous solid of Compound 41,043 (2.02 grams). This material could not be induced to crystallize.

COMPOUND 41,043

| Elementary Analysis (sample dried overnight in vacuo over phosphorus pentoxide at room temperature) | |
|---|---|
| C | 50.10 |
| H | 4.88 |
| N | 9.15 |
| S | 8.40 |
| 0 | 27.47 (by difference) |

Optical Rotation $\alpha_D + 77°$ (c = 1.0, acetone)

| Ultraviolet Absorption Maxima | | | |
|---|---|---|---|
| EtOH | 225 | $E_{1\ cm}^{1\%}$ | 444 |
| γmax | 270 | | 217 |
| | 300sh | | 183 |
| | 350 nm | | 91 |

Characteristic Infrared Bands (KBr disc) in microns as shown in FIG. 1

3.00, 3.45, 5.72, 5.80, 5.90, 6.00, 6.45, 6.52, 7.22, 7.60, 8.00, 8.30, 8.60, 8.95, 9.35, 9.98, 10.15, 11.00, 12.68, and 13.35.

Solubilities

Soluble in acetone, chloroform, methylisobutyl ketone, ethyl acetate, ethanol, dimethyl sulfoxide and dimethylformamide; insoluble in hexane, heptane, water and diethyl ether.

A 2.5 gram portion of the material rich in Compound 41,494 (from the initially chromatographed 100 gram mixture of antibiotics) was applied to a 2.54 × 92 cm silica gel $PF_{254}$ column and eluted with chloroform:ethanol (90:10% v/v). All fractions were assayed by thin-layer chromatography and the appropriate column cuts pooled to afford 0.67 grams of Compound 41,494 as an amorphous solid. This material could not be induced to crystallize.

COMPOUND 41,494

| Elementary Analysis (sample dried in vacuo over phosphorus pentoxide at room temperature.) | |
|---|---|
| C | 49.94 |
| H | 4.80 |
| N | 9.29 |

-continued

| Elementary Analysis (sample dried in vacuo over phosphorus pentoxide at room temperature.) | |
|---|---|
| S | 8.46 |
| O | 27.52 (by difference) |

Optical Rotation $\alpha_D + 29°$ (c = 0.5, acetone)

Characteristic Infrared Bands (KBr disc) in microns as shown in FIG. 2

3.00, 3.45, 5.72, 5.78, 6.00, 6.55, 6.75, 7.25, 7.60, 8.02, 8.40, 8.60, 9.00, 9.25, 10.17, 10.40, 11.15, 12.60 and 13.35.

| Ultraviolet Absorption Maxima | | | |
|---|---|---|---|
| EtOH γmax | 270 | $E_{1\ cm}^{1\%}$ | 241 |
| | 295 sh | | 224 |
| | 350 nm | | 114 |

Solubilities

Soluble in acetone, chloroform, methylisobutylketone, ethyl acetate, ethanol, dimethyl sulfoxide and dimethylformamide; insoluble in hexane, heptane, water and diethyl ether.

What is claimed is:

1. An antibiotic complex produced by cultivating *Pseudonocardia fastidiosa* sp. nov. Routien ATCC 31181 under submerged aerobic conditions in an aqueous nutrient medium containing an assimilable source of carbon and nitrogen until substantial antibiotic activity is obtained and separating said antibiotic complex therefrom.

2. Antibiotic substance Compound 41,043 which is soluble in acetone, chloroform, methylisobutyl ketone, ethyl acetate, ethanol dimethyl sulfoxide or dimethylformamide; insoluble in hexane, heptane, water or diethyl ether; has absorption maxima in ethanol in the ultraviolet light region of the spectrum at 225, 270, 300 and 350 nm with $E_{1\ cm}^{1\%}$ values of 444, 217, 183 and 91, respectively; has the average composition by weight of 50.10% carbon, 4.88% hydrogen, 9.15% nitrogen, 8.40% sulfur and 27.50% oxygen (by difference); has an optical roration of $\alpha_D + 77°$ (c = 1.0, acetone); and when pelleted in KBr exhibits characteristic absorption in the infrared region at the following wavelengths in microns: 3.00, 3.45, 5.72, 5.80, 5.90, 6.00, 6.45, 6.52, 7.22, 7.60, 8.00, 8.30, 8.60, 8.95, 9.35, 9.98, 10.15, 11.00, 12.68 and 13.35.

3. Antibiotic substance Compound 41,494 which is soluble in acetone, chloroform, methylisobutyl ketone, ethyl acetate, ethanol, dimethyl sulfoxide or dimethylformamide; insoluble in hexane, heptane water or diethyl ether; has absorption maxima in ethanol in the ultraviolet light region of the spectrum at 270, 295 and 350 nm with $E_{1\ cm}^{1\%}$ values of 241, 224 and 114, respectively; has the average composition by weight of 49.94% carbon, 4,80% hydrogen, 9.29% nitrogen, 8.46% sulfur and 27.52% oxygen (by difference); has an optical rotation of $\alpha_D + 29°$ (c =0.5, acetone); and when pelleted in KBr exhibits characteristic absorption in the infrared region at the following wavelengths in microns: 3.00, 3.45, 5.78, 5.90, 6.00, 6.55, 6.75, 7.25, 7.60, 8.02, 8.40, 8.60, 9.00, 9.25, 10.17, 10.40, 11.15, 12.60 and 13.35.

* * * * *